United States Patent
Yang et al.

(10) Patent No.: US 7,456,205 B2
(45) Date of Patent: Nov. 25, 2008

(54) BENZOPYRAN COMPOUNDS, PROCESS FOR PREPARING THE SAME AND THEIR USE

(75) Inventors: Yushe Yang, Shanghai (CN); Lei Tang, Shanghai (CN); Ruyun Ji, Shanghai (CN); Kaixian Chen, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 169 days.

(21) Appl. No.: 10/546,872

(22) PCT Filed: Feb. 26, 2003

(86) PCT No.: PCT/CN03/00151

§ 371 (c)(1), (2), (4) Date: Nov. 18, 2005

(87) PCT Pub. No.: WO2004/076437

PCT Pub. Date: Sep. 10, 2004

(65) Prior Publication Data

US 2006/0178405 A1    Aug. 10, 2006

(51) Int. Cl.
*A61K 31/422* (2006.01)
*C07D 413/12* (2006.01)
*C07D 407/12* (2006.01)

(52) U.S. Cl. ........................ 514/374; 548/236
(58) Field of Classification Search ................. 548/236; 514/374

See application file for complete search history.

(56) References Cited

FOREIGN PATENT DOCUMENTS

| CN | 1218049 | 6/1996 |
|---|---|---|
| CN | 1183412 | 6/1998 |
| CN | 1359383 | 7/2002 |
| JP | 3-240783 | 10/1991 |

OTHER PUBLICATIONS

Madhavan et al., "Novel Coumarin, etc.," Bioorgainc & Medicinal Chemistry letters 13 (2003) 2547-2551.*

Swaroop et al., "Synthesis of 3-(3,3-Dimethylallyl)xanthyletin", *Indian Journal of Chemistry*, vol. 22B, Feb. 1983, pp. 105-108.

* cited by examiner

*Primary Examiner*—Patricia L Morris
(74) *Attorney, Agent, or Firm*—Nixon & Vanderhye P.C.

(57) ABSTRACT

The invention relates to the benzopyran compounds of formula (I), or the salts thereof, in which, the bond between 3 and 4 positions is a single or double bond; $R_1$ represents a hydrogen atom or a $C_{1-6}$ alkyl that can be substituted; $R_2$ represents a hydrogen atom, a $C_{1-6}$ alkyl that can be substituted or an aromatic carbocyclic or aromatic heterocyclic group that can be substituted. The invention also relates to a process for preparing such compounds or their salts as well as the use of such compounds or their salts in the preparation of the medicine against type II diabetes mellitus.

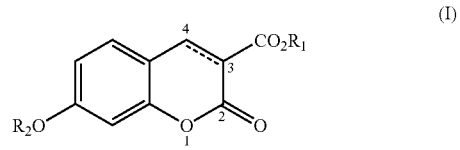

(I)

3 Claims, No Drawings

BENZOPYRAN COMPOUNDS, PROCESS FOR PREPARING THE SAME AND THEIR USE

FIELDS OF INVENTION

The invention relates to the fields of pharmaceutical chemistry and endocrinotherapy, and particularly to the synthesis of benzopyran compounds and their use in preparation of the medicine against type II disbetes mellitus.

BACKGROUND ART

Type II disbetes mellitus is a metabolic disturbance disease, and the patients exhibit mainly the symptoms of increased blood sugar concentration (the fasting blood sugar concentration is over 130 mg/dL) and glycosuria. Long-term hyperglycemia may cause the occurrence of various complicating diseases, such as pathological changes in the retina, the kidney and the nervous system. Among others, the cardiovascular complicating diseases are the main cause of the diabetic patients being dead or disabled [Shinkai, H. *Exp. Opin. Ther. Patents.* 2000, 10: 596]. Therefore, it is very important to control the patients' blood sugar concentration for inhibiting or blocking the occurrence of the complicating diseases. Currently, the sulfonylurea drugs for stimulating the scretion of insulin and the biguanide drugs are used clinically to control the patients' blood sugar concentration. Since the insulin resistance is the main pathogenesis of the type II diabetes mellitus, the insulin-sensitizing agent is an important trend in the research of drugs against the type II diabetes mellitus. The first thiozolidinedione insulin-sensitizer, troglitazone, is presented on the market in 1997. This drug as well as other drugs of the same kind available on the market later, pioglitazone and rosiglitazone, can control clinically the patients' blood sugar concentration well. However, the thiozolidinedione drugs exhibit the hepatotoxicity of different extents [Henry, R. R. *Endocrinol. Metab. Clin. North Am.* 1997, 26, 553]. And the troglitazone is withdrawn from the market due to its serious hepatotoxicity. The toxicity of this type of compounds was suspected to be related to the thiazolidinedione group. So the study of insulin-sensitizers has shifted to the synthesis and development of non-thiazolidinedione compounds for antitype II diabetes treatment.

One object of the present invention is to provide the novel benzopyran compounds with the insulin-sensitizing activities and the pharmaceutical acceptable salts thereof.

Another object of the present invention is to provide the preparative methods for the benzyopyran compounds and their salts.

A further object of the present invention is to provide the application of the benzopyran compounds and their salts in the preparation of the drugs against type II diabetes mellitus.

Methods of treating type II disbetes with the compounds of the present invention are also described herein.

SUMMARY OF THE INVENTION

The invention provides the benzopyran compounds represented by the following formula (I) and their salts:

(I)

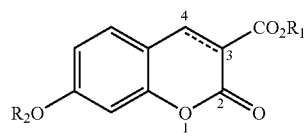

wherein, the bond between the 3 and 4 positions in the formula (I) is a single bond or a double bond;

$R_1$ = a hydrogen atom or a linear or branched $C_1$—$C_6$ alkyl;
$R_2$ = a linear or branched $C_1$—$C_6$ alkyl, or an aromatic ring or aromatic heterocyclic group selected from

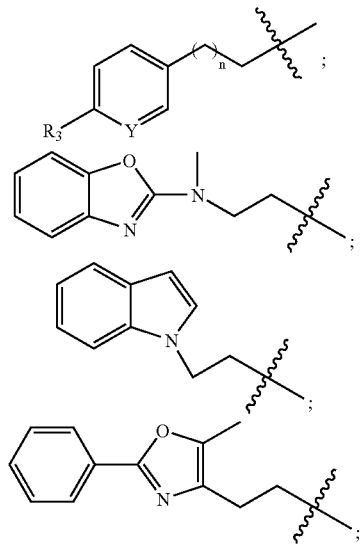

wherein $R_3$ is a linear or branched $C_1$—$C_4$ alkyl, trifluoromethyl, amino group, amino alkyl, nitryl, halogen or hydroxyl, n = 0-4, Y = N, CH.

The present invention further provides three preparative methods for the benzopyran compounds represented by the formula (I) and their salts.

The first preparative method includes the following steps:

(1) Conducting an etherification of 7-hydroxyl-3-coumarin carboxylic acid methyl ester and halogenated benzyl, followed by hydrolyzation under basic condition to give the compounds of formula (I), wherein $R_1$ is $CH_3$ or H, and $R_2$ is

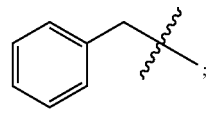

(2) Conducting Mitsunobu reaction of 7-hydroxyl-3-coumarin carboxylic acid methyl ester and corresponding alcohols, followed by hydrolyzation to obtain the compound of formula (I), wherein $R_1$ is $CH_3$ or H, and $R_2$ is

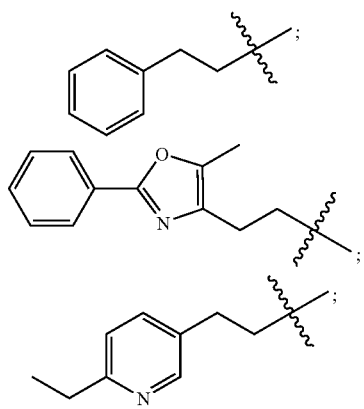

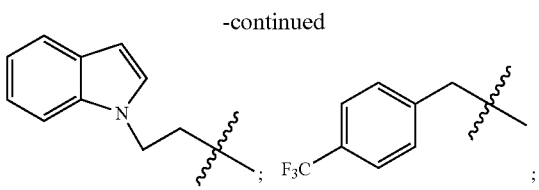

(3) Conducting catalytic hydrogenolysis of the compounds of formula (1) with the double bond between 3 and 4 positions, to obtain the compounds of formula (1) with the single bond between 3 and 4 positions;

(4) Preparing the corresponding pharmaceutical acceptable salts in a manner known in the art.

The second preparative method includes the following steps:

(1) Mitsunobu condensing 7-hydroxyl-3-coumarin carboxylic acid methyl ester with t-butoxylcarbony-protected 2-methylaminoethanol, deprotecting after hydrogenizing the resultant compounds to reduce the double bond, and condensing with 2-chlorobenzooxazole, wherein $R_1$ is $CH_3$, $R_2$ is

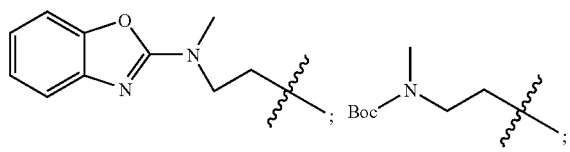

(2) Preparing the corresponding pharmaceutical acceptable salts in a manner known in the art.

The third preparative method includes the following steps:

(1) Mitsunobu condensing 7-hydroxyl-3-coumarin formic acid tert-butyl ester with 2-(5-methyl-2-phenyl-4-oxazole) ethanol, followed by catalytic hydrogenation of the resultant compounds to obtain the compounds of formula (I), wherein $R_1$ is tert-butyl or H, and $R_2$ is

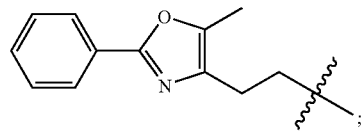

(2) Preparing the corresponding pharmaceutical acceptable salts in a manner known in the art.

The present invention further provides the application of the benzopyran compounds of formula (I) in the preparation of the drugs against type II diabetes mellitus.

DESCRIPTION OF THE INVENTION

Unless specified, the terms in the description have the following definitions:

The phrase "$C_{1-6}$ alkyl" includes the saturated or unsaturated, substituted or unsubstituted linear or branched alkane-derived groups containing 1 to 6 carbon atoms. Specific examples include methyl, ethyl, propyl, isopropyl, butyl, isobutyl, sec-butyl, tert-butyl, amyl, isoamyl, neo-pentyl, tert-amyl, 1-methylbutyl, 2-methylpropyl, hexyl, isohexyl, 1-methylamyl, 2-methylamyl, 3-methylamyl, 2-methylbutyl, 1,1-dimethylbutyl, 1,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or the like. Among these groups, the alkyls of 1 to 4 carbon atoms, such as methyl, ethyl, propyl, isopropyl, butyl or the like, are preferable. And methyl, ethyl, propyl are more preferable, methyl and ethyl are the most preferable.

The term "aryl" means an aromatic group, preferably an aryl of 6 to 14 carbon atoms, and including phenyl, tolyl, xylyl, biphenyl, naphthyl, indenyl, anthryl, phenanthryl, wherein phenyl and naphthyl are more preferable, and phenyl is the most preferable.

The term "aromatic heterocyclic group" means five- or six-membered hetero aromatic group containing 1-4 hetero atoms selected from oxygen, nitrogen and sulfur, and including furyl, thienyl, pyrrolyl, imidazolyl, thiazolyl, pyrazolyi, isothiazolyl, isoxazolyl, pyridyl, pyrimidinyl, pyridazinyl, pyrazinyl, triazolyl, tetrazolyl or the like. Among these groups, thienyl, furyl, oxazolyl, isoxazolyl and thiazolyl are preferable, and thienyl, oxazolyl and isoxazolyl are more preferable.

The term "substituted alkyl", "substituted aryl" and "substituted aromatic heterocyclic group" mean that the above "alkyl", "aryl" and "aromatic heterocyclic group" can be optionally substituted by the groups selected from halogen atoms, alkyl, alkoxyl, acyloxy, —OH, —NH$_2$, —NO$_2$, or —NHAc.

The "pharmaceutical acceptable salts" may specifically include the salts with inorganic acids, such as hydrochloric acid, hydrobromic acid, hydrofluoric acid, sulfuric acid, nitric acid, phosphoric acid or the like; the acid-addtion salts with organic acids, such as formic acid, acetic acid, propionic acid, oxalic acid, malonic acid, succinic acid, fumaric acid, maleic acid, lactic acid, malic acid, tartaric acid, citric acid, picric acid, methanesulfonic acid, ethylsulfonic acid or the like, and with acidic amino acids, such as aspartic acid, glutamic acid or the like; or the salts formed with alkalis, such as the salts with inorganic alkalis of Na, K, Ca, Al or the like, ammonium salt, methylamine salt, ethylamine salt, ethanolamine salt or the like; or the salts formed with basic amino acids, such as lysine, arginine, ornithine or the like.

The benzopyran compounds of formula (I) and their salts in the present invention are prepared as follows:

Procedure I:

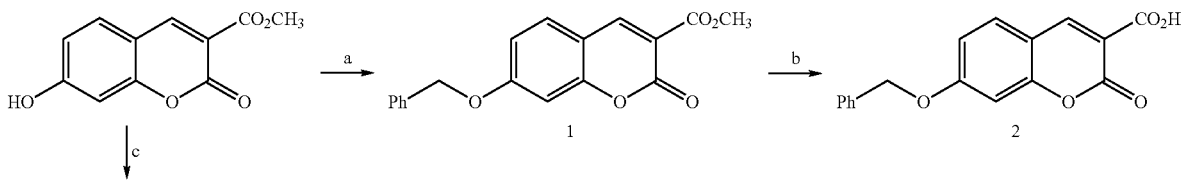

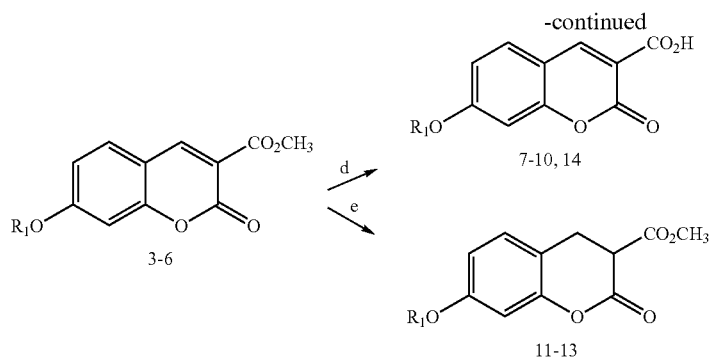

In the scheme: a. halogenated benzyl, inorganic alkali; b. hydrolyzation under the basis conditions, followed by acidification; c. $R_1$—OH, triphenylphosphine, diethyl azodicarboxylate; d. hydrolyzation under the basis conditions, followed by acidification; e. catalytic hydrogenolysis.

An embodiment of procedure I is as follows:

(1) Reacting 2, 4-dihydroxyl benzaldehyde with methyl malonic acid to obtain 7-hydroxyl-3-coumarin carboxylic acid methyl ester, which in turn reacts with halogenated benzyl under the basic condition to obtain the compound 1. The suitable halogenated benzyls for the condensation reaction are chlorobenzyl, bromicbenzyl, or the like, and the suitable inorganic bases are sodium hydroxide, lithium hydroxide, potassium hydroxide, sodium carbonate, potassium carbonate, lithium carbonate, etc. The condensation reaction temperature is between −10-180° C. The suitable solvents are the polar aprotic solvents, such as dimethylformamide, DMSO, etc. The reaction time is 0.1-72 hours. The optimal condensation reaction condition is to react 7-hydroxyl-3-coumarin carboxylic acid methyl ester with the bromicbenzyl in dimethylformamide, with the potassium carbonate as the base, at 70° C. for 0.1-12 hours.

The compound 1 is hydrolyzed under the basic condition, followed by acidification, to obtain the compound 2. The suitable inorganic bases for the hydrolyzation are sodium hydroxide, lithium hydroxide, potassium hydroxide, sodium carbonate, potassium carbonate, lithium carbonate, etc. The hydrolyzation temperature is between −10-200° C. The solvents are polar protic solvents, such as methanol, ethanol, water, etc, or the mixed solvent obtained by mixing them in proportion. The reaction time is 0.1-72 hours. The optimal hydrolyzation condition is to conduct the reaction with reflux in the 10% of sodium hydroxide aqueous solution for 1 hour. The suitable acids for acidification may be the inorganic acid, such as hydrochloric acid, sulfuric acid, nitric acid, phosphoric acid or the like, or the organic acid, such as acetic acid, maleic acid, citric acid, tartaric acid, or the like.

(2) Conducting the Mitsunobu reaction of 7-hydroxyl-3-coumarin carboxylic acid methyl ester and corresponding alcohols to obtain the compounds 3 to 6. The solvents used in the Mitsunobu reaction are the anhydrous inert solvents, such as anhydrous tetrahydrofuran, anhydrous dioxane, anhydrous benzene, anhydrous ether, chloroform, dichloromethane or the like. The reaction temperature is between −10-100° C., the reaction time is between 0.1-72 hours. The rude product is recrystallized with methanol, ethanol, isopropanol, ethyl acetate, chloroform and dichloromethane, or with the mixed solvent of two or more of them in proportion. The optimal reaction condition is to conduct the reaction under room temperature for 0.1-24h with the anhydrous tetrahydrofuran as solvent, and recrystallize the rude product with methanol.

(3) Hydrolyzing the compounds 3 to 6 under the suitable condition to obtain the compounds 7 to 10 and 14. The suitable inorganic bases for the hydrolyzation are sodium hydroxide, lithium hydroxide, potassium hydroxide, sodium carbonate, potassium carbonate, lithium carbonate, etc. The hydrolyzation temperature is between 0-150° C. The solvents are the polar protic solvents, such as methanol, ethanol, isopropanol water, or the like, the polar aprotic solvents, such as dimethylformamide and dimethylsulfoxide, or the mixed solvents of them in proportion. The reaction time is 0.1-72 hours. The optimal hydrolyzation condition is to conduct the reaction with reflux in the 10% of sodium hydroxide aqueous solution for 1 hour. The suitable acids for acidification are inorganic acid, such as hydrochloric acid, sulfuric acid, nitric acid, phosphoric acid or the like, or organic acid, such as acetic acid, maleic acid, citric acid, tartaric acid, or the like.

(4) Hydrogenolysing catalytically the compounds 3 to 6 to obtain the compounds 11 to 13. The catalysts for catalytic hydrogenolysis may be selected from the 10% or 5% of palladium-carbon or Raney-Ni or other catalysts containing palladium or nickel, and 10% of palladium-carbon is preferable. The solvents may be selected from the lower alkyl alcohols, such as methanol, ethanol, isopropanol, etc, or other solvents, such as acetic acid, anhydrous tetrahydrofuran, anhydrous dioxane, water, or the mixed solvents of two or more of them in suitable proportion. The reaction time is from 0.1 hours until no hydrogen is absorbed. The reaction temperature is from the room temperature to 40° C., and the room temperature is the most preferable. The reaction pressure ranges from the normal pressure to scores of atmospheric pressures, and the normal pressure is the most preferable. The solvents for recrystallization is ethanol, methanol, isopropanol, acetone, ethyl acetate, chloroform, dichloromethane, phenyl, toluene, n-hexane, n-heptane or the mixed solvents which are constituted by two or more of them in a suitable proportion. The preferable solvent for recrystallization of each compound is as showed in the embodiment.

(5) Preparing the corresponding pharmaceutical acceptable salts according to requirement.

Procedure II:

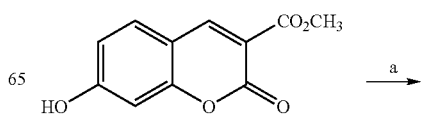

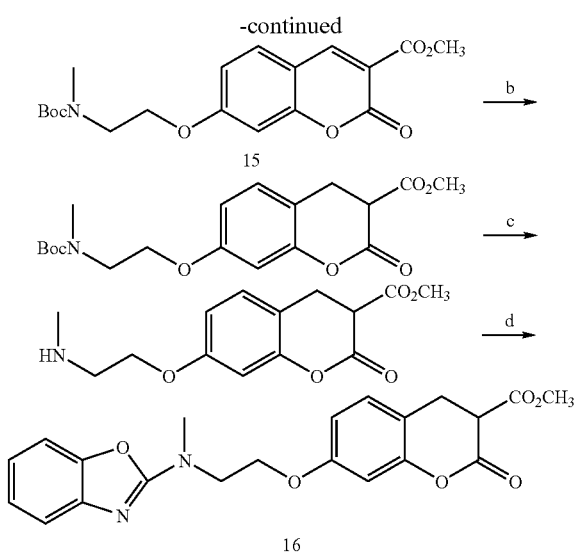

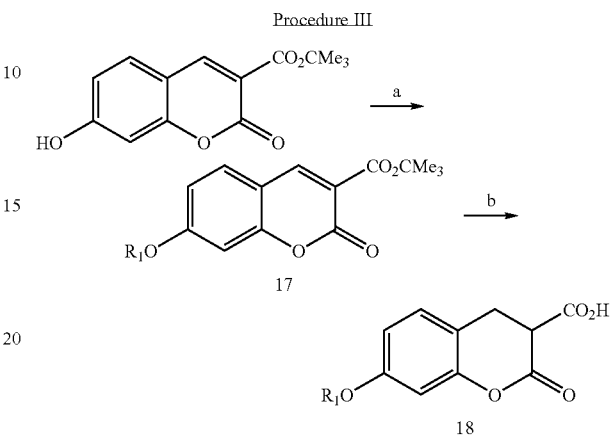

In the scheme: a. triphenylphosphine, diethyl azodicarboxylate, 2-(N-tert-carbobutoxy-N-methylamino)ethanol, tetrahydrofuran; b. $H_2$/Pd—C; c. trifluoroacetic acid, $CH_2Cl_2$; d. 2-chlorobenzoxazole.

An embodiment of procedure II is as follows:

(1) Conducting the Mitsunobu condensation of 7-hydroxyl-3-coumarin carboxylic acid methyl ester and t-butoxycarbonyl-protected 2-methylaminoethanol to obtain the compound 15. The solvents used in the Mitsunobu reaction are the anhydrous inert solvents, such as anhydrous tetrahydrofuran, anhydrous dioxane, anhydrous benzene, anhydrous ether, chloroform, dichloromethane or the like, and the anhydrous tetrahydrofuran is preferable. The reaction temperature is between −10-100° C., and the room temperature is preferable. The reaction time is between 0.1-72 hours, and 24 hours is the most preferable.

(2) Deprotecting after the compound 15 is hydrogenized to reduce the double bond, and then condensing with 2-chlorobenzoxazole to obtain the compound 16. The catalysts for catalytic hydrogenation may be selected from the 10% or 5% of palladium-carbon or Raney-Ni or other catalysts containing palladium or nickel, and 10% of palladium-carbon is preferable. The solvents may be selected from the lower alkyl alcohols, such as methanol, ethanol, isopropanol, etc, or other solvents, such as acetic acid, anhydrous tetrahydrofuran, anhydrous dioxane, water, or the mixed solvents constituted by two or more of them in suitable proportion. The reaction time is from 0.1 hours until no hydrogen is absorbed. The reaction temperature is from the room temperature to 40° C., and the room temperature is the most preferable. The reaction pressure ranges from the normal pressure to scores of atmospheric pressures, the normal pressure is the most preferable.

Removal of the protective group can be conducted by stirring with trifluoroacetic acid for 48 hours at −10-80° C. The optimal reaction condition is to stir with trifluoroacetic acid for 8 hours at 0° C.

The suitable inorganic bases for condensation with 2-chlorobenzoxazole include sodium hydroxide, lithium hydroxide, potassium hydroxide, sodium carbonate, potassium carbonate, lithium carbonate, etc. or the organic bases include triethylamine, pyridine, diisopropylamine, etc. The hydrolyzation temperature is −10-150° C. The solvents are the polar aprotic solvents, such as tetrahydrofuran, ether, benzene, chloroform, dichloromethane, DMF, DMSO, etc. The reaction time is 0.1-72 hours.

(3) Corresponding pharmaceutical acceptable salts are prepared according to requirement.

In the scheme: a. $R_1$—OH, triphenylphosphine, diethyl azodicarboxylate; b. i. $H_2$/Pd—C; ii. trifluoroacetic acid, $CH_2Cl_2$.

An embodiment of procedure III is as follows:

(1) 2,4-dihydroxyl benzaldehyde and tert-butyl malonic acid are reacted to obtain 7-hydroxyl-3-coumarin formic acid tert-butyl ester, which in turn is Mitsunobu condensed with 2-(5-methyl-2-phenyl-4-oxazole)ethanol to obtain the compound 17. The solvents used in Mitsunobu reaction are the anhydrous inert solvents, such as anhydrous tetrahydrofuran, anhydrous dioxane, anhydrous benzene, anhydrous ether, chloroform, dichloromethane or the like, and the anhydrous tetrahydrofuran is preferable. The reaction temperature is between −10-100° C., and the room temperature is preferable. The reaction time is between 0.1-72 hours, and 24 hours are preferable.

(2) The compound 17 is catalytically hydrogenated to obtain the compound 18. The catalysts for catalytic hydrogenation may be selected from the 10% or 5% of palladium-carbon or Raney-Ni or other catalysts containing palladium or nickel, and 10% of palladium-carbon is preferable. The solvents may be selected from the lower alkyl alcohols, such as methanol, ethanol, isopropanol, etc, or the polar aprotic solvents, such as tetrahydrofuran, dioxane, ether, etc, or other solvents, such as acetic acid, water, etc. or the mixed solvents constituted by two or more of the above solvents in suitable proportion, and the mixed solvent of methanol/dioxane in the ratio of 1:1 is the most preferable. The reaction time is from 0.5 hours until no hydrogen is absorbed. The reaction temperature is from the room temperature to 40° C., and the room temperature is the most preferable. The reaction pressure ranges from the normal pressure to scores of atmospheric pressures, the normal pressure is the most preferable.

Removal of the protective group can be conducted by stirring with trifluoroacetic acid for 48 hours at −10-80° C. The optimal reaction condition is to stir with trifluoroacetic acid for 8 hours at 0° C.

(3) Corresponding pharmaceutical acceptable salts are prepared according to requirement.

The representative benzopyran compounds of formula (I) according to the present invention are listed as follows:s (1) 7-benzyloxyl-2-oxo-2H-1-benzopyran-3-carboxylic acid methyl ester;

(2) 7-benzyloxyl-2-oxo-2H-1-benzopyran-3-carboxylic acid;

(3) 7-(2-phenyl)ethoxyl-2-oxo-2H-1-benzopyran-3-carboxylic acid methyl ester;

(4) 7-[2-(5-ethyl-2-pyridine)ethyoxyl]-2-oxo-2H-1-benzopyran-3-carboxylic acid methyl ester;

(5) 7-[2-(1-indole)ethoxyl]-2-oxo-2H-1-benzopyran-3-carboxylic acid methyl ester;

(6) 7-[2-(5-methyl-2-phenyl-4-oxazole)ethoxyl]-2-oxo-2H-1-benzopyran-3-carboxylic acid methyl ester;

(7) 7-(2-phenyl)ethoxyl-2-oxo-2H-1-benzopyran-3-carboxylic acid;

(8) 7-[2-(5-ethyl-2-pyridine)ethyoxyl]-2-oxo-2H-1-benzopyran-3-carboxylic acid;

(9) 7-[2-(1-indole)ethoxyl]-2-oxo-2H-1-benzopyran-3-carboxylic acid;

(10) 7-[2-(5-methyl-2-phenyl-4-oxazole)ethoxyl]-2-oxo-2H-1-benzopyran-3-carboxylic acid;

(11) 7-(2-phenyl)ethoxyl-3,4-dihydro-2-oxo-4H-1-benzopyran-3-carboxylic acid methyl ester;

(12) 7-[2-(5-ethyl-2-pyridine)ethyoxyl]-3,4-dihydro-2-oxo-4H-1-benzopyran-3-carboxylic acid methyl ester;

(13) 7-[2-(5-methyl-2-phenyl-4-oxazole)ethoxyl]-3,4-dihydro-2-oxo-4H-1-benzopran-3-carboxylic acid methyl ester;

(14) 7-(4-trifluoromethylbenzyloxyl)-3,4-dihydro-2-oxo-4H-1-benzopyran-3-carboxylic acid methyl ester;

(15) 7-[2-(N-tert-butoxycarbonyl-N-methylamino)ethoxyl]-2-oxo-2H-1-benzopyran-3-carboxylic acid methyl ester;

(16) 7-[2-[N-methyl-N-(2-benzoxazole)amino]ethoxyl]-3,4-dihydro-2-oxo-4H-1-benzopyran-3-carboxylic acid methyl ester;

(17) 7-[2-(5-methyl-2-phenyl-4-oxazole)ethoxyl]-2-oxo-2H-1-benzopyran-3-carboxylic acid tert-butyl ester;

(18) 7-[2-(5-methyl-2-phenyl-4-oxazole)ethoxyl]-3,4-dihydro-2-oxo-4H-1-benzopyran-3-carboxylic acid.

The structure formulas of the above-mentioned compounds 1-18 see table 1.

TABLE 1

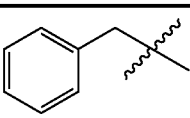

| Compound No. | R2 | R1 | Double bond between positions 3 and 4$^a$ |
|---|---|---|---|
| 1 | 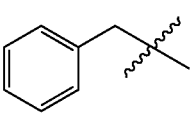 | CH$_3$ | Yes |
| 2 | 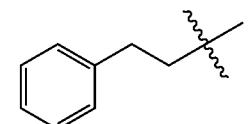 | H | Yes |

TABLE 1-continued

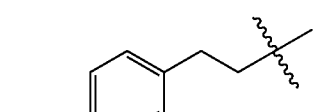

| Compound No. | R2 | R1 | Double bond between positions 3 and 4$^a$ |
|---|---|---|---|
| 3 | 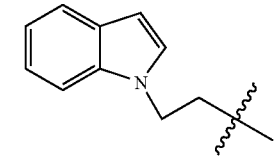 | CH$_3$ | Yes |
| 4 | 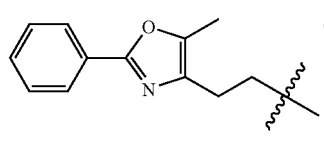 | CH$_3$ | Yes |
| 5 | 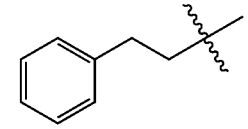 | CH$_3$ | Yes |
| 6 | 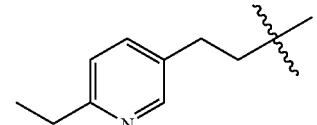 | CH$_3$ | Yes |
| 7 | 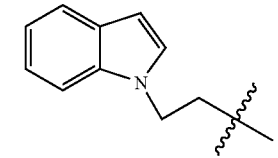 | H | Yes |
| 8 | 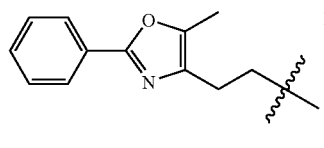 | H | Yes |
| 9 | 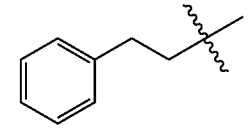 | H | Yes |
| 10 | | H | Yes |
| 11 | | CH$_3$ | No |

TABLE 1-continued

Structure: 7-R2O-coumarin-3-CO2R1

| Compound No. | R2 | R1 | Double bond between positions 3 and 4[a] |
|---|---|---|---|
| 12 | 6-ethyl-pyridin-3-yl-ethyl | CH3 | No |
| 13 | 2-phenyl-5-methyl-oxazol-4-yl-ethyl | CH3 | No |
| 14 | 4-(trifluoromethyl)benzyl | CH3 | No |
| 15 | BocNH-CH(CH3)-ethyl | CH3 | Yes |
| 16 | benzoxazol-2-yl-N(CH3)-ethyl | CH3 | No |
| 17 | 2-phenyl-5-methyl-oxazol-4-yl-ethyl | t-Bu | Yes |
| 18 | 2-phenyl-5-methyl-oxazol-4-yl-ethyl | H | No |

[a]Yes: double bond between positions 3 and 4; No: single bond between positions 3 and 4

Evaluation of biological activities:

The insulin-sensitizing agents can promote the differentiation of pre-adipocytes toward adipocyte. Thus insulin-sensitizing agents could be identified with the insex of the differentiation of pre-adipocytes. Following the methods reported in the literature [Kletzein B F. Mol. Pharm. 1991, 41, 393], the insulin-sensitizing activities of the compounds of formula (I) of the present invention were evaluated in 3T3-L1 preadipocyte model with triglyceride accumulation in cells as the indication of cell differentiation.

The 3T3-L1 cells were incubated in DMEM (Dulbecco's Modified Eagle's Medium) containing 10% NBS (newborn calf serum) and subcultured every 3 days. The cells were transferred to 24-pore plates, and after the pores were filled completely, the cells were treated with IBMX (isobutylmethylxanthine) (0.5 mmol/L), DEX (dexamethasone) (1 μmol/L) and insulin (1.0 μmol/L) for 48 h, meanwhile different amounts of test compounds were added into. The cells were incubated continuously until the end of the experiment. Cells were collected and the contents of triglyceride and protein therein were determined by colorimetry. Enhancements of triglyceride in cells after drug-administrating were calculated.

The positive control group was rosiglitazone, and the solvent control group was a culturing medium containing 0.1% of DMSO. The enhancement of triglyceride in cells of three different concentrations (0.01, 0.1, 1 μmol/L) of each tested compounds is presented in Table 2, from which it can be see that the compounds 6, 13, 17, 18, etc have stronger insulin-sensitizing activity. Thus, the derivatives of the benzopyran compounds of the present invention can be used to control the blood glucose level in type II diabetes patients and inhibit the occurrence of complications caused by the type II diabetes.

The benzopyran compounds of the present invention do not contain a thiazolidinedione group, but possess the similar insulin-sensitizing activity as that of the thiazolicinedione compounds. Therefore, it is possible that the compounds disclosed herein will be developed as the novel medicaments for treatment of type II diabetes.

TABLE 2

The Percentage of Triglyceride Increased in 3T3-L1 Cells

| | Concentration of the test compounds (μmol/L) | | |
|---|---|---|---|
| Compound No. | 0.01 | 0.1 | 1 |
| 1 | −5.73 | −0.43 | 7.93 |
| 2 | 20.86 | 18.31 | 14.63 |
| 3 | 4.57 | −2.61 | −5.50 |
| 4 | 7.26 | 11.55 | 17.71 |
| 5 | 7.88 | 27.58 | 34.74 |
| 6 | 27.04 | 67.24 | 52.45 |
| 7 | 7.97 | −1.10 | −6.29 |
| 8 | 12.25 | 3.67 | 5.66 |
| 9 | −5.25 | −8.42 | −12.95 |
| 10 | −3.28 | 26.68 | 32.30 |
| 11 | −9.13 | 12.90 | 14.10 |
| 12 | 4.13 | −2.40 | 2.53 |
| 13 | 28.33 | 52.92 | 64.69 |
| 14 | 19.33 | −16.81 | −2.69 |
| 15 | 26.38 | 26.73 | 44.70 |
| 16 | 11.01 | 29.32 | 25.09 |
| 17 | 18.33 | 28.20 | 33.01 |
| 18 | 18.65 | 29.28 | 30.24 |
| Rosiglitazone[b] | 27.20 ± 2.35 | 34.93 ± 2.14 | 39.21 ± 2.27 |

[a]Average data in 3 pores.
[b]Sample number n = 22;
The value in the table is the mean value of enhancement of triglyceride ± SD.
ND: Not Done.

The compounds of the present invention and their pharmaceutical acceptable salts may be prepared into many forms of preparations, which contain a safe and effective dosage of the compounds or their pharmaceutical acceptable salts in the present invention, and the pharmaceutical acceptable carrier.

"Safe and effective dosage" means the amount of the compounds that are sufficient to improve significantly the condition of patients, but do not lead to serious side effects. The safe and effective dosage of compounds is determined according to the age, condition, and course of treatment of the subjects accepting the therapy and will usually be determinable by one of ordinary skill by routine experimentation.

"Pharmaceutical acceptable carrier" refers to one or many kinds of compatible solid or liquid packing materials or gelling substances, which are suitable for human use and have enough purity and low toxicity. "compatible" is used to indicate that each component in the compositions can mixed with the compounds of the present invention and with each other without significantly impairing the drug action of the compounds. Some examples of the pharmaceutical acceptable carrier include cellulose and its derivatives (CMC—Na, EC—Na, cellulose acetic acid ester etc.), gelatin, steatite, solid lubricants (such as stearic acid, magnesium stearate), $CaSO_4$, vegetable oils (such as soya oil, sesame oil, peanut oil, olive oil etc.), polybasic alcohol (such as propylene glycol, glycerin, mannitol, sorbierite etc.), emulsifying agent (such as tweens®), moistening agent (such as sodium dodecylsulfate), coloring agent, flavoring agent, stabilizer, antioxidant, antiseptic, pyrogen-free water, etc.

THE PREFERABLE EMBODIMENTS OF THE INVENTION

The present invention will be further explained with reference to the following examples, but they don't limit the present invention in any way. In all examples, the melting points were measured with MEL-TEMP melting point apparatus and the thermometer was not calibrated; $^1$H NMR spectra were recorded on a Varian Mercury 400 NMR spectrometer, the chemical shifts are expressed as δ (ppm); silica gel for separation is 200-300 mesh unless otherwise specified.

EXAMPLE 1

7-benzyloxyl-2-oxo-2H-1-benzopyran-3-carboxylic acid methyl ester (compound 1)

7-hydroxyl-3-coumarin carboxylic acid methyl ester (0.2g, 1 mmol) is dissolved in N,N'-dimethyl formamide (2 mL), and bromobenzyl (0.36 ml, 3 mmol) and levigated potassium carbonate (0.5 g) are added into. The resulting mixture is stirred for 12 hours at 70° C. After adding 10 mL of water, extraction is conducted with ethyl acetate, and all of ethyl acetate are combined, followed by washing with water, drying on anhydrous sodium sulfate. Then the solution is concentrated under reduced pressure to approximately 5 mL and is placed to separate out a solid, followed by filtering under reduced pressure to obtain 0.21 g of the captioned compound, yield: 67.7%. m.p.129-130° C. $^1$H NMR(CDCl$_3$): δ=3.92(s, 3H), 5.19(s, 2H), 6.85(d, J=2.4 Hz, 1H), 6.95(dd, J=8.8 Hz, 2.4 Hz, 1H), 7.40(m, 5H), 7.52(d, J=8.8 Hz, 1H), 8.55(s, 1H); Elements Analysis, $C_{18}H_{14}O_5$ (310): Calculated C, 69.68; H, 4.52. Found C, 69.63; H, 4.51; IR(KBr): 3054.7, 2948.7, 1749.1, 1697.1, 1610.3, 1558.2, 1500.4, 1438.7, 1378.9, 1226.5, 1116.6, 1026, 794.5, 725.1, 692.3, 636.4 cm$^{-1}$; EI-MS(m/z): 310(12, M$^+$), 91(100).

EXAMPLE 2

7-benzyloxyl-2-oxo-2 H-1-benzopyran-3-carboxylic acid (compound 2)

The compound 1 (0.1 g, 0.32 mmol) is dissolved in ethanol (0.5 mL), and 10% of sodium hydroxide aqueous solution (0.5 mL) is added into. The resulting mixture is reacted for 1 hour with reflux. After cooling, the strong hydrochloric acid (0.3 mL) is added and followed by stirring for 10 minutes. 5 mL of water is added, and produced solid is obtained by filtration. The filter cake is washed with water, followed by drying to obtain 0.09 g of the captioned compound, yield: 90%. m.p. 196-197° C. $^1$H NMR (DMSO-d6): δ=5.25(s, 2H), 7.08(dd, J=2.2 Hz, 8.8 Hz, 1H), 7.12(d, J=2.2 Hz, 1H), 7.30-7.50(m, 5H), 7.83(d, J=8.8 Hz, 1H), 8.73(s, 1H); Elements Analysis, $C_{17}H_{12}O_5$ (296): Calculated C, 68.92; H, 4.05; Found C, 68.50; H, 4.12; IR(KBr): 3054.7, 1747.2, 1677.8, 1600.7, 1556.3, 1421.3, 1378.9, 1257.4, 1209.2, 1120.2, 732.8 cm$^{-1}$; EI-MS(m/z): 296(4, M$^+$), 91(100).

EXAMPLE 3

7-(2-phenyl)ethoxyl-2-oxo-2H-1-benzopyran-3-carboxylic acid methyl ester (compound 3)

7-hydroxyl-3-coumarin carboxylic acid methyl ester (0.6g, 3 mmol) and 2-phenyl ethanol (0.36 mL, 3 mmol) are dissolved in anhydrous tetrahydrofuran (60 mL). Triphenylphosphine (1.2 g, 4.5 mmol) is added, and diethyl azodicarboxylate (0.72 mL, 4.5 mmol) is added dropwise and slowly at 0° C. The resulting solution is stirred for 24 hours at room temperature. After the solvent was removed under reduced pressure, the residue is diluted with methanol and a white solid is separated out. The solid is recrystallized with methanol to give 0.45 g of the captioned compound, yield: 46.3%. m.p. 100-101° C. $^1$H NMR(CDCl$_3$): δ=3.12(t, J=6.8 Hz, 2H), 3.92(s, 3H), 4.14(t, J=7.1 Hz, 2H), 6.79(d, J=2.4 Hz, 1H), 6.88(dd, J=2.4 Hz, 8.8 Hz, 1H), 7.21-7.35(m, 5H), 7.47 (d, J=8.7 Hz, 1H), 8.50(s, 1H); Element Anyalysis, $C_{19}H_{16}O_5$ (324): Calculated C, 70.37; H, 4.94. Found C, 70.25; H, 4.93; IR(KBr): 3045.1, 2952.5, 1751.1, 1693.2, 1610.3, 1554.4, 1506.2, 1436.7, 1375, 1307.5, 1222.7, 1114.7, 1018.2, 835, 749.5, 738.6, 700, 594 cm$^{-1}$; EI-MS(m/z): 324(24, M$^+$), 105 (100).

EXAMPLE 4

7-[2-(5-ethyl-2-pyridine)ethyoxyl]-2-oxo-2H-1-benzopyran-3-carboxylic acid methyl ester (compound 4)

With 2-(5-ethyl-2-pyridine)ethanol and 7-hydroxyl-3-coumarin carboxylic acid methyl ester as starting material, the captioned compound was prepared by the same method as in example 3, yield: 50.5%. m.p. 99-100° C. $^1$H NMR(CDCl$_3$): δ=1.24(t, J=7.7 Hz, 3H), 2.65(m, J=7.7 Hz, 2H), 3.28(t, J=6.6 Hz, 2H), 3.92(s, 3H), 4.45(t, J=6.6 Hz, 2H), 6.80(d, J=2.2 Hz, 1H), 6.90(dd, J=8.5 Hz, 2.2 Hz, 1H), 7.20(d, J=8.0 Hz, 1H), 7.45(d, J=8.5 Hz, 1H), 7.55(dd, J=7.9 Hz, 2.2 Hz, 1H), 8.40 (d, J=2.2 Hz, 1H), 8.55(s, 1H); Element Analysis, $C_{20}H_{19}NO_5$ (353): Calculated C, 67.99; H, 5.38; N, 3.97. Found C, 67.96; H, 5.43; N, 3.87; IR(KBr): 2696.9, 1758.8, 1693.2, 1616.1, 1560.2, 1442.5, 1376.9, 1309.4, 1226.5, 1114.7, 1022.1, 792.6, 590.1 cm$^{-1}$; EI-MS(m/z): 277(100), 353(8, M$^+$).

EXAMPLE 5

7-[2-(1-indole)ethoxyl]-2-oxo-2H-1-benzopyran-3-carboxylic acid methyl ester (compound 5)

With 2-(1-indole)ethanol and 7-hydroxyl-3-coumarin carboxylic acid methyl ester as staring material, the rude product of the captioned compound was prepared by the same method as in example 3, and the rude product is insoluble in the methanol. The rude product is refluxed with menthol for 10 minutes, and then cooled down, followed by filtrating under reduced pressure to give the captioned compound, yield: 72.1%. m.p. 136-137° C. $^1$H NMR(CDCl$_3$): δ=3.90(s, 3H), 4.35(t, J=5.3 Hz, 2H), 4.58(t, J=5.3 Hz, 2H), 6.50(d, J=3.4 Hz, 1H), 6.71(d, J=2.4 Hz, 1H), 6.80(dd, J=2.0 Hz, 8.3 Hz, 1H), 7.10(t, J=7.3 Hz, 1H), 7.18(d, J=2.9 Hz, 1H), 7.21(m, 1H), 7.40(d, J=8.3 Hz ,1H), 7.43(d, J=8.8 Hz, 1H), 7.62(d, J=7.8 Hz, 1H), 8.48(s,1H); Element Analysis, $C_{21}H_{16}NO_5$ (362): Calculated C, 69.61; H, 4.42; N,3.34. Found C, 69.44; H, 4.69; N, 3.85; EI-MS(m/z): 363 (40, M$^+$+1), 130 (100).

EXAMPLE 6

7-[2-(5-methyl-2-phenyl-4-oxazole)ethoxyl]-2-oxo-2H-1-benzopyran-3-carboxylic acid methyl ester (compound 6)

2-(5-methyl-2-phenyl-4-oxazole)ethanol (0.38 g, 1.85 mmol) and 7-hydroxyl-3-coumarin carboxylic acid methyl ester (0.37 g, 1.85 mmol) are dissolved in anhydrous tetrahydrofuran (40 mL). Triphenylphosphine (0.726 g, 2.78 mmol) is added, and diethyl azodicarboxylate (438 μL, 2.78 mmol) is added dropwise and slowly at 0° C. The resulting solution is stirred for 24 hours at room temperature. After the solvent was removed under reduced pressure, the residue is diluted with methanol and a solid is separated out, followed by filtrating under reduced pressure to give 0.38 g of the captioned compound, yield: 51.3%. m.p. 139-140° C. (Decomposed). $^1$H NMR(CDCl$_3$): δ=2.36(s, 3H, oxazole-CH$_3$), 3.02(t, J=6.6 Hz, 2H, oxazole-CH$_2$—), 3.91(s, 3H, OCH$_3$), 4.34(t, J=6.5 Hz, 2H, H$_2$C—O), 6.80(d, J=2.2 Hz, 1H, 8-H), 6.85(dd, J=8.7 Hz, 2.3 Hz, 1H, 6-H), 7.40(m, 3H, Ph—H), 7.46(d, J=8.8Hz, 1H, 5-H), 7.96(m, 2H), 8.50(s, 1H, 4-H); Element Analysis, $C_{23}H_{19}NO_6$ (405): Calculated C, 68.15; H, 4.69; N, 3.46. Found C, 68.22; H, 4.98; N, 3.50; IR(KBr) : 3072.1, 1762.6, 1697.1, 1612.2, 1558.2, 1376.9, 1313.3, 1222.7, 1139.7, 1016.3, 709.7 cm$^{-1}$; EI-MS(m/z): 405(16, M$^+$), 186(100).

EXAMPLE 7

7-(2-phenyl)ethoxyl-2-oxo-2H-1-benzopyran-3-carboxylic acid (compound 7)

With the compound 3 as starting material, the captioned compound was prepared by the same method as in example 2, yield: 92%. m.p. 150-151° C. $^1$H NMR(DMSO-d6): δ=3.08 (t, J=6.8 Hz, 2H), 4.35(t, J=6.8 Hz, 2H), 6.98(dd, J=2.5 Hz, 8.5 Hz, 1H), 7.04(d, J=2.5 Hz, 1H), 7.18-7.34(m, 5H), 7.80(d, J=8.8 Hz, 1H), 8.70(s, 1H), 12.95(s, 1H, COOH); Element Analysis, $C_{18}H_{14}O_5$ (310): Calculated C, 69.68; H, 4.52. Found C, 69.55; H, 4.34; IR(KBr) :2952.5, 1741.4, 1679.7, 1618, 1556.3, 1425.2, 1382.7, 1257.4, 1213, 1122.4, 808, 698.1 cm$^{-1}$; EI-MS(m/z): 310(3, M$^+$), 105(100).

EXAMPLE 8

7-[2-(5-ethyl-2-pyridine)ethyoxyl]-2-oxo-2H-1-benzopyran-3-carboxylic acid (compound 8)

With the compound 4 as starting material, the captioned compound was prepared by the same method as in example 2, yield: 91%. m.p.130-131° C. $^1$H NMR(DMSO-d6): δ=1.28(t, J=7.5 Hz, 3H), 2.81(m, J=7.5 Hz, 2H), 3.53(m, 2H), 4.58(t, J=6.4 Hz, 2H), 6.95(dd, J=8.7 Hz, 2.0 Hz, 1H), 7.15(d, J=2.0 Hz, 1H), 7.80(d, J=8.7 Hz, 1H), 7.98(d, J=7.9 Hz, 1H), 8.40 (d, J=8.3 Hz,1H), 8.70(s, 1H), 8.75(s, 1H); Element Analysis, $C_{19}H_{17}NO_5$.2H$_2$O(375): Calculated C, 60.80; H, 5.60; N, 3.73. Found C, 60.34; H, 5.27; N, 3.70; IR(KBr) : 3548.4, 3477.1, 3369.1, 3045.1, 2969.9, 2630.5, 1741.4, 1689.4, 1612.2, 1556.3, 1540.2, 1382.7, 1226.5, 1180.2, 1016.3, 798.4 cm$^{-1}$; EI-MS(m/z): 339(8, M$^+$), 134(100).

EXAMPLE 9

7-[2-(1-indole)ethoxyl]-2-oxo-2H-1-benzopyran-3-carboxylic acid (compound 9)

With the compound 5 as starting material, the captioned compound was prepared by the same method as in example 2, yield: 91%. m.p. 166-168° C. $^1$H NMR(DMSO-d6): δ=4.42 (t, J=5.0 Hz, 2H), 4.60(t, J=5.3 Hz, 2H), 6.43(m, 1H), 6.90 (dd, J=2.4 Hz, 8.8 Hz, 1H), 7.00(m, 2H), 7.12(m, 1H), 7.41(d, J=3.3 Hz, 1H), 7.52(m, 2H), 7.78(d, J=8.8 Hz, 1H), 8.68(s, 1H), 12.98(s, 1H); Element Analysis, $C_{20}H_{14}NO_5$ (348): Calculated C, 68.97; H, 4.02; N, 4.02. Found C, 68.38; H, 4.36; N, 3.93; IR(KBr) : 3058.6, 2971.8, 1764.6, 1637.9, 1602.6, 1554.4, 1508.1, 1380.8, 1276.7, 1226.5, 1139.7, 800.3, 732.8 cm$^{-1}$; EI-MS(m/z): 349(9, M$^+$+1), 105(100).

EXAMPLE 10

7-[2-(5-methyl-2-phenyl-4-oxazole)ethoxyl]-2-oxo-2H-1-benzopyran-3-carboxylic acid (compound 10)

With the compound 6 as starting material, the captioned compound was prepared by the same method as in example 2, yield: 91%. m.p.142-143° C. $^1$H NMR(DMSO-d6): δ=2.38 (s, 3H, oxazole-CH$_3$), 2.78(t, J=6.8 Hz, 2H, —CH$_2$—C), 4.37(t, J=6.9 Hz, 2H, CH$_2$—O), 7.01(dd, J=2.5 Hz, 8.3 Hz, 1H, 6-H), 7.06(d, J=2.4 Hz, 1H, 8-H), 7.48(m, 3H, Ph—H), 7.81(d, J=8.8 Hz, 1H, 5-H), 7.90(m, 2H, Ph—H), 8.71(s ,1H, 4-H), 13.0(s, 1H, COOH); Element Analysis, $C_{22}H_{17}NO_6$.⅔H$_2$O(403): Calculated C, 65.51; H, 4.55; N, 3.47. Found C, 65.23; H, 4.41; N, 3.32; IR(KBr): 3054.7, 1749.1, 1679.7, 1554.4, 1508.1, 1378.9, 1257.4, 1211.1, 1141.7, 800.3, 690.4 cm$^{-1}$; EI-MS(m/z): 391(28, M$^+$), 91(100); HRMS: 391.1047 ($C_{22}H_{17}NO_6$).

EXAMPLE 11

7-(2-phenyl)ethoxyl-3,4-dihydro-2-oxo-4H-1-benzopyran-3-carboxylic acid methyl ester (compound 11)

The compound 3 (0.62 g, 1.58 mmol) is dissolved in the mixed solvent of methanol (3 mL) and dioxane (1 mL), and 10% of Pd—C (0.2 g) is added into the solution. The resulting solution is hydrogenized under the normal pressure until no further hydrogen is absorbed. The mixture is filtrated to remove Pd—C, and the solvent is removed under reduced pressure to give 0.6 g of the captioned compound, yield: 95%. $^1$H NMR(CDCl$_3$): δ=2.97(t, J=6.7 Hz, 2H), 3.10(dd, J=5.9 Hz, 15.8 Hz, 1H), 3.35(dd, J=8.8 Hz, 16.1 Hz, 1H), 3.75(m, 4H), 4.22(t, J=6.6 Hz, 2H), 6.70(d, J=2.3 Hz, 1H), 6.79(dd, J=8.8 Hz, 2.3 Hz, 1H), 6.98(d, J=8.8 Hz, 1H), 7.43(m, 3H), 7.99(m, 2H); Element Analysis, $C_{19}H_{18}O_5$.⅓H$_2$O(332): Calculated C, 68.67; H, 5.62. Found C, 68.87; H, 5.71 ;IR(KBr) :3479, 2933.2, 1758.8, 1735.6, 1631.5, 1511.9, 1434.8, 1357.7, 1286.3, 1213, 1164.8, 1118.5, 1022.1, 759.8, 705.8, 609.4 cm$^{-1}$; EI-MS(m/z): 326(12, M$^+$), 105(100).

EXAMPLE 12

7-[2-(5-ethyl-2-pyridine)ethyoxyl]-3,4-dihydro-2-oxo-4H-1-benzopyran-3-carboxylic acid methyl ester (compound 12)

With the compound 4 as starting material, the captioned compound was prepared by the same method as in example 11, yield: 96%. m.p. 85-86° C. (decomposed). $^1$H NMR (CDCl$_3$): δ=1.24(t, J=7.7 Hz, 3H), 2.62(m, J=7.7 Hz, 2H), 3.15(dd, J=6.2 Hz, 15.9 Hz, 1H), 3.21(t, J=6.8 Hz, 2H), 3.35(dd, J=8.4 Hz, 15.9 Hz, 1H), 3.65(m, 4H), 4.30(t, J=6.8 Hz, 2H), 6.80(d, J=2.6 Hz, 1H), 6.88(dd, J=8.5 Hz, 2.6 Hz, 1H), 7.15(d, J=8.2 Hz, 1H), 7.20(d, J=8.1 Hz, 1H), 7.48(dd, J=7.9 Hz, 2.2 Hz, 1H), 8.40(d, J=2.0 Hz, 1H); Element Analysis, $C_{20}H_{21}NO_5$ (355): Calculated C, 67.61; H, 5.92; N, 3.94. Found C, 67.52; H, 5.84; N, 3.78; IR (KBr): 2960.2, 1700.4, 1737.6, 1629.6, 1510, 1434.8, 1371.2, 1292.1, 1203.4, 1161, 1124.3, 1031.7, 848.5, 800.3, 607.5 $cm^{-1}$; El-MS (m/z): 355 (4, $M^+$), 121(59), 134(100).

EXAMPLE 13

7-[2-(5-methyl-2-phenyl-4-oxazole)ethoxyl]-3,4-dihydro-2-oxo-4H-1-benzopyran-3-carboxylic acid methyl ester (compound 13)

The compound 6 (0.05 g, 0.14 mmol) is dissolved in the mixed solvent of methanol (1.5 mL) and dioxane (3 mL), and 10% of Pd—C (0.05 g) is added into the solution. The resulting solution is hydrogenized under the normal pressure until no further hydrogen is absorbed. The mixture is filtrated to remove Pd—C. After the solvent was removed under reduced pressure, the residue is diluted with methanol and a solid is separated out, followed by filtrating under reduced pressure to give 0.4 g of the captioned compound, yield: 80.0%. $^1$H NMR($CDCl_3$): δ=2.37(s, 3H), 2.97(t, J=6.5 Hz, 2H), 3.08(dd, J=15.9 Hz, 6.1 Hz, 1H), 3.34(dd, J=15.7 Hz, 8.6 Hz, 1H), 3.73(m, 4H), 4.22(t, J=6.4 Hz, 2H), 6.60(d, J=2.2 Hz, 1H), 6.64(dd, J=8.5 Hz, 2.3 Hz, 1H), 7.06(d, J=8.4 Hz, 1H), 7.41 (m, 3H), 7.99(m, 2H); Element Analysis, $C_{23}H_{21}NO_6$ (407): Calculated C, 67.81; H, 5.16; N, 3.44. Found C, 67.81; H, 5.16; N, 3.43; IR(KBr) : 2919.7, 1754.9, 1731.8, 1629.6, 1510, 1444.4, 1365.4, 1292.1, 1161, 1147.5, 1120.5, 800.3, 713.5, 686.5 $cm^{-1}$; EI-MS(m/z): 407(20, $M^+$), 186(100).

EXAMPLE 14

7-(4-trifluoromethylbenzyloxyl)-3,4-dihydro-2-oxo-4H-1-benzopyran-3-carboxylic acid methyl ester (compound 14)

4-trifluoromethylbenzalcohol (70 μL, 0.5 mmol) and 7-hydroxyl-3,4-dihydro-3-coumarin carboxylic acid methyl ester (0.1 g, 0.5 mmol) are dissolved in anhydrous ether (8 mL). Triphenylphosphine (0.19 g, 0.75 mmol) is added, and diethyl azodicarboxylate (120 μL, 0.75 mmol) is added dropwise and slowly at 0° C. The resulting solution is stirred for 24 hours at room temperature. After the solvent was removed under reduced pressure at 30° C., the residue is mixed with methanol at room temperature. A solid is produced by filtrating under reduced pressure and 0.12 g of the captioned compound is obtained, yield: 61%. m.p. 138-139° C. $^1$H NMR($CDCl_3$): δ=3.35(d, 13.6 Hz, 1H), 3.50(d, 13.8 Hz, 1H), 3.60(m, 4H), 5.09(s, 2H), 6.62(d, J=2.5 Hz, 1H), 6.70(dd, J=8.4 Hz, 2.3 Hz, 1H), 7.05(d, J=8.4 Hz, 1H), 7.40(d, J=8.3 Hz, 2H), 7.65(d, J=8.3 Hz, 2H); Element Analysis, $C_{19}H_{25}F_3O_5$(380): Calculated C, 60.00; H, 3.95. Found C, 60.43; H, 3.77; IR(KBr): 3068.2, 1768.4, 1724.1, 1625.7, 1510.0, 1332.6, 1243.9, 1162.9, 1068.4, 829.3 $cm^{-1}$; EI-MS(m/z): 380(4, $M^+$), 159 (100); HRMS: 380.0846($C_{19}H_{15}F_3O_5$).

EXAMPLE 15

7-[2-(N-tert-butoxycarbonyl-N-methylamino) ethoxyl]-2-oxo-2H-1-benzopyran-3-carboxylic acid methyl ester (compound 15)

2-(N-tert-butoxycarbonyl-N-methylamino)ethanol (0.5 g, 3 mmol) and 7-hydroxyl-3-coumarin carboxylic acid methyl ester (0.6 g, 3 mmol) are dissolved in 60 mL of anhydrous tetrahydrofuran. Triphenylphosphine (1.2 g, 4.5 mmol) is added, and diethyl azodicarboxylate (720 μL, 0.45 mmol) is added dropwise and slowly at 0° C. The resulting solution is stirred at room temperature for 24 hours. After the solvent was removed under reduced pressure at 30° C., the residue is mixed with methanol at room temperature. A solid is produced by filtrating under reduced pressure and 0.83 g of the captioned compound is obtained, yield: 72.6%. m.p. 128-129° C. $^1$H NMR(DMCO-d6): δ=1.40(s, 9H), 2.96(s, 3H), 3.65(s, 2H), 3.81(s, 3H), 4.32(s, 2H), 6.94(d, J=2.2 Hz, 1H), 7.00(dd, J=2.2 Hz, 8.4 Hz, 1H), 7.80(d, J=8.8 Hz, 1H), 8.60 (s,1H); EI-MS(m/z): 377(1, $M^+$), 102(100).

EXAMPLE 16

7-[2-[N-methyl-N-(2-benzoxazole)amino]ethoxyl]-3,4-dihydro-2-oxo-4H-1-benzopyran-3-carboxylic acid methyl ester (compound 16)

The compound 15 (0.55 g, 1.46 mmol) is dissolved in the mixed solvent of methanol (5 mL) and dioxane (15 mL), and 10% of Pd—C (0.1 g) is added into the solution. The resulting solution is hydrogenized under the normal pressure until no further hydrogen is absorbed. The mixture is filtrated to remove Pd—C, followed by removing the solvent under reduced pressure to give 0.54 g of the white-like solid. The solid is dissolved into the dichloromethane (1.7mL), followed by adding 1.7 mL of the trifluoracetic acid. The resulting mixture is stirred for 8 hours at 0° C. After removing a part of solvent under the reduced pressure at room temperature, the residue solution is adjusted to weak alkalescence with saturated $NaHCO_3$ aqueous solution and extracted with dichloromethane(2×10 mL). The combined dichloromethane were washed with $H_2O$, dried on anhydrous $MgSO_4$, and filtered under reduced pressure. The solvent is evaporated off from the filtrate to give 0.35 g of white solid. The solid is dissolved into tetrahydrofuran (5 mL), 2-chlorobenzoxazole (0.4 g, 2.6 mmol) and triethylamine (0.72 mL, 5.2 mmol) are added at 0° C. The mixture is stirred for 12 hours at room temperature. After the tetrahydrofuran is removed under the reduced pressure, the residue is dissolved in the ethyl acetate (10 mL), and washed with water (10 mL). The phase of ethyl acetate is separated, and dried on anhydrous sodium sulphate. After the ethyl acetate is removed under the reduced pressure, the residue is chromatographed over silica gel column with petroleum/ethyl acetate (3:4) as eluent to obtain 0.28 g of the captioned compound, yield: 50.1%. m.p. 88-90° C. $^1$H NMR ($CDCl_3$): δ=3.10(dd, J=6.1 Hz, 16.0 Hz, 1H), 3.33(m, 4H), 3.72(m, 4H), 3.92(t, J=5.2 Hz, 2H), 4.23(t, J=5.1 Hz, 2H), 6.61(d, J=2.6 Hz, 1H), 6.65(dd, J=2.4 Hz, 8.3 Hz, 1H), 7.00 (m, 1H), 7.08(d J=8.4 Hz, 1H), 7.16(m, 1H), 7.26(d, J=7.9 Hz, 1H), 7.36(d, J=7.8 Hz, 1H); Element Analysis, $C_{21}H_{20}N_2O_6$ (396): Calculated C, 63.60; H, 5.05; N, 7.07. Found C, 63.76; H, 5.00; N, 6.80; IR (KBr): 2935.2, 1768.4, 1735.6, 1648.9, 158.2, 1510, 1459.9, 1434.8, 1292.1, 1240, 1161, 1145.5, 1002.8, 800.3, 734.8 $cm^{-1}$; EI-MS(m/z): 396 (12, $M^+$), 148(100).

EXAMPLE 17

7-[2-(5-methyl-2-phenyl-4-oxazole)ethoxyl]-2-oxo-2H-1-benzopyran-3-carboxylic acid tert-butyl ester (compound 17)

2,4-dihydroxylbenzaldehyde (0.27 g, 2 mmol) and di-tert-buty malonic acid (0.43 g, 2 mmol) are dissolved in tert-butanol (5 mL), and three drops of piperidine are added. The mixture is refluxed for 16 hours to obtain a suspension. After being placed for cooling, insoluble material is removed by filtrating. The mother liquor is concentrated, and the ethyl acetate is added with stirring. The supernatant is separated, concentrated, and chromatographed over silica gel column with petroleum/ethyl acetate (3:4) as eluent to obtain 0.14 g of 7-hydroxyl-3-coumarin carboxylic acid tert-butyl ester, yield: 22.5%.

The captioned compound is produced by the same method as in example 6 with 2-(5-methyl-2-phenyl-4-oxazole) and 7-hydroxyl-3-coumarin carboxylic acid tert-butyl ester as the starting material yield: 36%. m.p.140-142° C. $^1$H NMR (DMCO-d6): δ=1.58(s, 9H), 2.42(s, 3H), 3.04(t, J=6.6 Hz, 2H), 4.46(t, J=6.6 Hz, 2H), 6.95(d, J=2.2 Hz, 1H), 6.99(dd, J=8.8 Hz, 2.2 Hz, 1H), 7.50(m, 3H), 7.73(d, J=8.4 Hz, 1H), 7.99(m, 2H), 8.53(s, 1H); Element Analysis, $C_{26}H_{25}NO_6$ (447): Calculated C, 69.80; H, 5.59; N, 3.13. Found C, 69.79; H, 5.57; N, 3.16; IR(KBr): 2979.5, 1747.2, 1708.6, 1612.2, 1508.1, 1371.2, 1226.5, 1164.8, 1014.4, 833.1, 690.4 cm$^{-1}$.

EXAMPLE 18

7-[2-(5-methyl-2-phenyl-4-oxazole)ethoxyl]-3,4-dihydro-2-oxo-4H-1-benzopyran-3-carboxylic acid (compound 18)

The compound 17 (70 mg, 1.56 mmol) is dissolved in the mixed solvent of methanol/dioxane (1:1) (8 mL), and 10% of Pd—C (0.05 g) is added into the solution. The resulting solution is hydrogenized under the normal pressure until no further hydrogen is absorbed. The mixture is filtrated to remove Pd—C, followed by removing the solvent under reduced pressure to obtain a oily substance (0.05 g). 0.01 g of the oily substance is dissolved into the dichloromethane (0.5 mL), followed by adding 0.5 mL of the trifluoracetic acid. The resulting mixture is stirred for 1 hour at room temperature. After removing a part of solvent under the reduced pressure, 5 mL of water is added into the residue solution, followed by extracting with ethyl acetate (2×5 mL). The combined ethyl acetate were washed with $H_2O$, dried on anhydrous $MgSO_4$, and filtered. The filtrate is concentrated into approximately 3 mL, and is placed at −20° C. to give white precipitate. The precipitate is filtered under reduced pressure and dried to give 7 mg of the captioned compound, yield: 13%. m.p. 124-125° C. $^1$H NMR(DMSO-d6): δ=2.37(s, 3H), 2.91(t, J=6.6 Hz, 2H), 3.18(m, 2H), 3.92(t, J=6.2 Hz, 1H), 4.22(t, J=6.6 Hz, 2H), 6.72(m, 2H), 7.20(d, J=8.1 Hz, 1H), 7.50(m, 3H), 7.90 (m, 2H); Element Analysis, $C_{22}H_{19}NO_6 \cdot \frac{1}{2} H_2O$ (402): Calculated C, 65.67; H, 4.98; N, 3.48. Found C, 66.04; H, 4.87; N, 3.34; IR (KBr): 2923.6, 1738.4, 1627.7, 1511.9, 1288.2, 1120.5, 850.5, 713.5 cm$^{-1}$; EI-MS(m/z): 349(52), 186(100).

INDUSTRIAL APPLICABILITY

The present invention provides benzopyran compounds or salts thereof which have the higher insulin-sensitizing activities similar to those of thiozolidinedione compounds, but the compounds of the present invention don't comprise the thiozolidinedione group. Thus, the benzopyran compounds of the present invention may be developed into the novel drugs for diabetes without the hepatic toxicity, which are used to control the high blood glucose level and inhibit the occurrence of the complications caused by the diabetes.

What is claimed is:

1. A benzopyran compound of formula (I) or its salt:

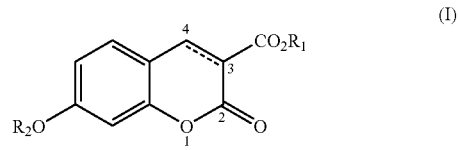

wherein, the bond between the 3 and 4 position in the formula (I) is a single bond or a double bond;

$R_1$ = a hydrogen atom or a linear or branched $C_1$-$C_6$ alkyl; and $R_2$ = an aromatic heterocyclic group represented by the following formula:

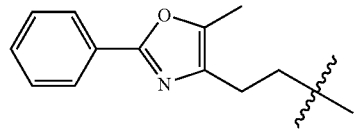

2. A benzopyran compound of formula (I) or its salt of claim 1, which compound is selected from the group consisting of:

(1) 7-[2-(5-methyl-2-phenyl-4-oxazole)ethoxyl]-2-oxo-2H-1-benzopyran-3-carboxylic acid methyl ester; (2) 7-[2-(5-methyl-2-phenyl-4-oxazole)ethoxyl]-2-oxo-2H-1-benzopyran-3 -carboxylic acid; (3) 7-[2-(5-methyl-2-phenyl-4-oxazole)ethoxyl]-3,4-dihydro-2-oxo-4H-1-benzopyran-3-carboxylic acid methyl ester; (4) 7-[2-(5-methyl-2-phenyl-4-oxazole)ethoxyl]-2-oxo-2H-1-benzopyran-3 -carboxylic acid tert-butyl ester; and (5) 7-[2-(5-methyl-2-phenyl-4-oxazole)ethoxyl]-3,4-dihydro-2-oxo-4H- 1 -benzopyran-3 -carboxylic acid.

3. A method of treating type II diabetes mellitus comprising administering to a subject an effective amount of a compound of claim 1.

* * * * *